(12) United States Patent
Spillert et al.

(10) Patent No.: US 7,094,428 B2
(45) Date of Patent: Aug. 22, 2006

(54) HEMOSTATIC COMPOSITIONS, DEVICES AND METHODS

(75) Inventors: Charles R. Spillert, West Orange, NJ (US); Marcelle Khalil, Morganville, NJ (US)

(73) Assignee: The University of Medicine and Dentistry of New Jersey, New Brunswick, NJ (US)

( * ) Notice: Subject to any disclaimer, the term of this patent is extended or adjusted under 35 U.S.C. 154(b) by 304 days.

(21) Appl. No.: 10/315,918

(22) Filed: Dec. 10, 2002

(65) Prior Publication Data

US 2003/0129183 A1 Jul. 10, 2003

Related U.S. Application Data

(63) Continuation of application No. PCT/US01/19145, filed on Jun. 15, 2001.
(60) Provisional application No. 60/212,229, filed on Jun. 16, 2000.

(51) Int. Cl.
*A61K 9/14* (2006.01)
*A61K 33/38* (2006.01)
*A61K 38/36* (2006.01)
*A61F 2/00* (2006.01)
*A61F 13/00* (2006.01)

(52) U.S. Cl. ............... 424/489; 424/423; 424/443; 424/445; 424/618; 424/644; 424/94.64

(58) Field of Classification Search ............... 424/422, 424/423, 426, 424, 430, 431, 434, 443, 445, 424/446, 447, 489, 644, 618, 94.64
See application file for complete search history.

(56) References Cited

U.S. PATENT DOCUMENTS 4,891,359 A   1/1990  Saferstein et al.
5,595,735 A   1/1997  Saferstein et al.
5,948,425 A   9/1999  Janzen et al.
5,951,583 A   9/1999  Jensen et al.
6,245,573 B1  6/2001  Spillert

FOREIGN PATENT DOCUMENTS

DE      3523023         1/1987
EP      0 956 869 A2   11/1999
JP      05-017369       1/1993
WO      WO 99/04828 A3  2/1999
WO      WO 99/04828 A2 * 2/1999

OTHER PUBLICATIONS

Hiroshi Kaneko, et al., Mercury Compounds induce a rapid increase in procoagulant activity of monocyte–like U937 cells, British Journal of Haematology, vol. 87, pp. 87–93.
Christopher A. Goodwin, et al., Increased expression of procoagulant activity on the surface of human platelets exposed to heavy–metal compounds; vol. 308, pp. 15–21.

* cited by examiner

*Primary Examiner*—James M. Spear
(74) *Attorney, Agent, or Firm*—Klauber & Jackson (57) ABSTRACT

A hemostatic composition which comprises at least one procoagulant metal ion, such as silver (I) or mercury (II), and at least one procoagulant biopolymer, such as collagen, thrombin, prothrombin, fibrin, fibrinogen, heparinase, Factor VIIa, Factor VIII, Factor IXa, Factor Xa, Factor XII, von Willebrand Factor, a selectin, a procoagulant venom, a plasminogen activator inhibitor, glycoprotein IIb-IIIa, a protease, or plasma. The composition in the form of a paste, dough, glue, liquid, lyophilized powder or foam, may be provided, for application to a wound. A hemostatic device is also described which comprises a hemostatic composition as described above. The device may be in the form of, for example, a plug, bandage, gauze, cloth, tampon, membrane or sponge. Methods are also provided for prophylaxis or treatment of bleeding at a site by application to the site of the composition or device as described.

3 Claims, 7 Drawing Sheets

FIG. 1

FIG. 4
EFFECT OF Ag+, COLLAGEN AND HEPARIN ON CLOTTING OF PLASMA

HEMOSTATIC COMPOSITIONS, DEVICES AND METHODS

This application is a continuation of international application No. PCT US01/19145, filed Jun. 15, 2001 which claims benefit of provisional application 60/212,229 filed Jun. 16, 2000 (status, abandoned, pending, etc.).

BACKGROUND OF THE INVENTION

Uncontrolled hemorrhage from any type of wound, whether accidental or iatrogenic, may result in dire consequences. In particular, bleeding attendant with arterial damage is particularly troublesome, especially in an individual with a coagulopathy, congenital, the result of disease, or induced by administration of anticoagulants. Moreover, recovery from surgical and other procedures involving transarterial cannulation, particularly in anticoagulated individuals, presents a challenge to the medical profession as such individuals often present prolonged bleeding times from such wounds, necessitating close monitoring and increased length of hospital or in-patient stays. In such patients, manual pressure, pressure bandages, sandbags, and other means have been used to hasten hemostasis at the wound site. Not only is the excessive bleeding potentially dangerous to the patient, but the burden of the excess attention to the wound is dangerous to the already overburdened health care system.

The foregoing discussion is also pertinent to arterial and other major hemorrhagic wounds suffered from traumatic injury such as those inflicted on the battlefield, as a result of vehicular accidents, and from knife and gunshot wounds. Means to stop potentially fatal hemorrhage outside of the hospital environment is desirable.

Numerous hemostatic agents, compositions, and devices are known. Many such agents and compositions employ naturally procoagulant biopolymers, such as clotting factors and connective tissue proteins that have known hemostatic roles in vivo. Devices may include an inflatable member for blocking an opening in an artery, at which site a hemostatic agent may be introduced; other devices comprise agents or compositions in a particular form for application to a hemorrhaging site or plugging a puncture-type wound. For example, U.S. Pat. No. 5,951,583 describes lyophilized thrombin, reconstituted with buffer and mixed with collagen, to form a viscous mixture. U.S. Pat. No. 4,891,359 describes a hemostatic collagen paste composition, which optionally includes thrombin. U.S. Pat. No. 5,595,735 described a hemostatic composition comprising thrombin in a polyethylene glycol base. U.S. Pat. No. 5,948,425 described a hemostatic plug comprising collagen for sealing an incision which comprises a bleeding blood vessel. These and all other citations herein are incorporated herein by reference in their entireties.

Certain metal ions have known hemostatic properties. The use of silver nitrate as a topically applied cautery agent is known. As described in copending application Ser. No. 09/022,449, filed Feb. 12, 1998, now U.S. Pat. No. 6,245,573, metal ions such as mercuric ion, silver ion, ion, cadmium ion, copper ion, barium ion, tin ion, selenate ion and tungstate ion are useful to modulate the clotting rate of blood in order to diagnose coagulopathies. Silver metal, in the form of colloidal silver, has been used as an antimicrobial agent for many years, predating the use of antibiotics, but still used today particularly in the management of burn patients.

It is toward the development of improved hemostatic compositions and devices that the present invention is directed.

The citation of any reference herein should not be construed as an admission that such reference is available as "Prior Art" to the instant application.

SUMMARY OF THE INVENTION

In its broadest aspect, the present invention is directed to a hemostatic composition which comprises at least one procoagulant metal ion and at least one procoagulant biopolymer. The metal ion may be, by way of non-limiting example, silver (I) or mercury (II). Preferably, silver (I) ion is used. Such ions, particularly silver, may be used at very low concentrations, for example, as low as the level of free silver ion available from an insoluble silver salt such as silver chloride. The procoagulant biopolymer may be, for example, one or more of the following: collagen, thrombin, prothrombin, fibrin, fibrinogen, heparinase, Factor VIIa, Factor VIII, Factor IXa, Factor Xa, Factor XII, von Willebrand Factor, a selectin, a procoagulant venom, a plasminogen activator inhibitor, glycoprotein IIb-IIIa, proteases, or plasma. The hemostatic composition of the invention may also include a carrier, such as, but not limited to, polyethylene glycol, hyaluronic acid, methyl cellulose, or albumin. In a preferred embodiment, the concentration of the metal ion present in the biopolymer may be reduced below its effective hemostatic concentration in the absence of the biopolymer, as the instant inventors have found surprisingly a synergy between the procoagulant biopolymer and the procoagulant metal ion. In another embodiment, the level of the procoagulant biopolymer may be reduced well below its effective hemostatic concentration in the absence of the metal ion. In a further embodiment, the hemostatic composition comprises a procoagulant polymer at a sub-coagulant level in the absence of a metal ion, in combination with a metal ion at a sub-coagulant level in the absence of a procoagulant polymer.

The hemostatic composition of the invention may be in the form of, for example, a paste, dough, glue, liquid, lyophilized powder or foam, for application to a wound.

In another aspect, the invention is directed to a hemostatic device which comprises a hemostatic composition as described above. The device may be in the form of, for example, a plug, bandage, gauze, cloth, tampon, membrane or sponge.

A method for the prophylaxis or treatment of bleeding at a site is provided herein by applying to the site a hemostatic composition as described above, or a hemostatic device as described above. In one embodiment, the methods and compositions of the invention are useful in treating hemorrhaging, hypothermic patients.

The present invention is further directed to a method for the prophylaxis or treatment of bleeding at a site by applying to the site a composition comprising at least one procoagulant metal ion and at least one procoagulant biopolymer. The procoagulant metal ions and biopolymers are as described hereinabove. The composition may include a carrier, as described above. The hemostatic composition of the invention may be in the form of, for example, a paste, dough, glue, liquid, lyophilized powder or foam. Other forms of the composition are embraced herein.

In another aspect, the invention is directed to a method for the prophylaxis or treatment of bleeding at a site by applying to the site a device comprising a composition comprising at least one procoagulant metal ion and at least one procoagulant biopolymer. The procoagulant metal ions and procoagulant biopolymers are as described hereinabove. As noted above, the device may be in the form of a plug, bandage, gauze, cloth, tampon, membrane or sponge. Other forms of the device are embraced herein.

These and other aspects of the present invention will be better appreciated by reference to the following drawings and Detailed Description.

DETAILED DESCRIPTION OF THE INVENTION

The present invention is broadly directed to hemostatic compositions and devices comprising at least one procoagulant metal ion and at least one procoagulant biopolymer, optionally with a carrier. Although silver (I) ion has been used as a cautery agent to stop bleeding by direct application of a soluble silver salt such as silver nitrate to a wound, it was found herein by surprise that an improved hemostatic composition was preparable using the combination of at least one procoagulant metal ion, such as silver (I) ion, and at least one procoagulant biopolymer, such as collagen. Furthermore, the inventor has found that the combination of a low concentrations of a procoagulant metal ion and a procoagulant biopolymer provides an effective hemostatic composition at concentrations wherein the individual components alone are less or not at all effective. For example, the concentration of free silver ion available in a composition of the invention comprising what is generally regarded as the water-insoluble silver salt silver chloride is adequate to promote hemostasis in combination with a procoagulant polymer. Thus, a composition of the present invention achieves the desired hemostatic activity with low concentrations of components, offering less potential toxicity, more rapid biodegradation, lower cost of raw materials, and superior activity in wound dressings and arterial plugs. A further advantage is that the clot formed in the presence of the instant compositions are stronger than clots formed in the absence of the compositions.

The inventor has found that the present procoagulant compositions are useful for inducing clotting in both whole blood and in plasma. As will be seen below, the procoagulant properties of the present compositions are also useful in the presence of anticoagulant factors such as heparin. As patients undergoing anticoagulant therapy are prone to prolonged and thus dangerous bleeding, the present compositions are particularly useful for use in surgery or trauma care in such patients.

The invention has been described in co-pending provisional application Ser. No. 60/212,229, filed Jun. 16, 2000, and is incorporated herein by reference in its entirety. Moreover, priority of the present application is claimed to the aforementioned provisional application under 35 U.S.C. § 119(e). As shown therein, various metal ions at low concentrations in combination with a procoagulant biopolymer were found to act synergistically to promote coagulation or clotting of whole blood.

Further studies herein have confirmed and expanded the scope of the invention. Measurements of the procoagulant effects of the compositions of the invention have been carried out using a SONOCLOT miniviscometer to detect early clot formation. In such studies, anti-coagulated, citrated whole blood is recalcified to initiate the clotting process in a device which sensitively monitors the formation of the clot. Studies have been expanded from whole blood to include plasma.

Various metal ions known to have procoagulant properties are useful in the compositions and devices of the present invention. The present invention embraces all such procoagulant metal ions. These ions are set forth herein as the element followed by the number of positive charges of the ion in parentheses, such as silver (I) or mercury (II) [also known as mercuric]. Any salts of these ions are suitable for use intended herein that provide a effective procoagulant level of free metal ion. Using silver (I) as an example, the nitrate salt provides adequate free silver (I) ion, whereas the chloride salt provides less, being less soluble and with a low dissociation constant. However, as mentioned above, certain metal salts which are considered insoluble have a large-enough dissociation constant to permit an effective procoagulant level of the metal ion to be present in the compositions herein which comprise the insoluble metal salt. The skilled artisan will be able to readily determine the suitable salt form of the metal ion that provides the procoagulant properties in combination with the procoagulant biopolymer. Furthermore, the skilled artisan will be aware of the compatibility of the salt forms of the metal(s) and other components of the composition to maintain adequate levels of the metal ion(s) in solution to provide procoagulant activity. Of course, considerations must be given to the toxicity of the metal salt, whether soluble or not, at the concentrations needed for an effective hemostatic composition.

As noted herein, the composition may comprise one or more procoagulant metal ions, such as silver (I) or mercury (II). For the example of silver (I) ion, effective levels may be achieved by using water-soluble silver salts such as the nitrate, selenate, nitrite, or perchlorate salts, or organic acids such as lactate. In the case of mercury (II), nitrate, acetate and chloride salts are examples. Mercury (II) ion in the form of MERCUROCHROME(R) (2',7'-dibromo-5-[hydroxymercuric]fluorescein) may also be used. As noted above, when such salts are used in combination, one must be cognizant of the compatibilities of the salts to avoid reducing the solubility of the procoagulant ion(s) below their effective concentration(s). Furthermore, certain components may provide oxidative or reductive properties which in contact with the metal ion(s), may alter their oxidation state and effectiveness. Such considerations are well within the realm of the skilled artisan in preparing an effective procoagulant composition in accordance with the disclosure herein.

As noted above, a composition of the present invention may have more than one metal salt, such as the combination of silver (I) and mercury (II).

With regard to the procoagulant biopolymer of the instant composition, this component embraces naturally occurring, recombinant, isolated, and any and all other forms of procoagulant proteins and other biologically compatible polymers with procoagulant activity. By way of non-limiting example, procoagulant proteins embraced herein include but are not limited to collagen, thrombin, prothrombin, fibrin, fibrinogen, heparinase, Factor VIIa, Factor VIII, Factor IXa, Factor Xa, Factor XII, von Willebrand Factor, a selectin, a procoagulant venom, a plasminogen activator inhibitor, glycoprotein IIb-IIIa, proteases, or plasma. These may be used singly or in combination. Such proteins include those which have a net effect of procoagulant activity, such as clot dissolution inhibitors including plasminogen activator inhibitor. Included herein is plasma, which comprises numerous procoagulant proteins, and proteases, which are procoagulant. An example of a procoagulant venom is Russells' viper venom. Examples of proteases are described in the catalog of Sigma Chemical Company, from numerous sources.

The procoagulant proteins of the invention may be prepared by any of numerous methods or obtained from commercial sources. Many-such proteins are available in purified form, for example, from Sigma Chemical Co., American Diagnostica, and Critichem Inc., to name only a few examples.

A preferred procoagulant polymer is collagen, and more preferred, type I collagen. It is available from any of a number of sources in various forms, including fibrillar, amorphous, and others. Particular preparations used for certain of the studies herein are sponge collagens, woven collagens and fibrillar collagens from the Collagen Products Division of Datascope Corp., Mahwah, N.J., U.S.A.

The concentrations of the procoagulant metal ion(s) and procoagulant biopolymer(s) in the composition of the invention may be prepared in accordance with the desired properties of the composition, the form of the device in which the composition is delivered or applied to the wound, and other factors that one or ordinary skill in the art would take into account in preparing the composition or device of the invention. Of course, the composition must have low toxicity, and if left in place, preferably needs to biodegrade after it has achieved its desired function. As noted above, it was found that the concentration of the procoagulant metal ion(s) in the instant composition may be reduced to a level below which it would not be effective as the sole hemostatic agent. For example, for a particular sample of patient blood, a composition comprising silver (I) and collagen may comprise 1% collagen and 0.1% silver nitrate, wherein 0.1% silver nitrate alon[]e would not impart significant hemostasis in a wound. Therefore, the hemostatic compositions of the present invention may, in one embodiment, include either the procoagulant biopolymer or the procoagulant metal ion, or both, at a concentration lower than would be hemostatically effective alone.

Examples of suitable compositions of the invention comprising one procoagulant biopolymer include, but are not limited to, silver (I) and collagen, silver (I) and thrombin, silver (I) and prothrombin, silver (I),and fibrin, silver (I) and fibrinogen, silver (I) and heparinase, silver (I) and Factor VIIa, silver (I) and Factor VIII, silver (I) and Factor IXa, silver (I) and Factor Xa, silver (I) and Factor XII, silver (I) and von Willebrand Factor, silver (I) and a selectin, silver (I) and a procoagulant venom, silver (I) and a plasminogen activator inhibitor, silver (I) and glycoprotein IIb-IIIa, silver (I) and a protease, silver (I) and plasma; mercury (II) and collagen, mercury (II) and thrombin, mercury (II) and prothrombin, mercury (II) and fibrin, mercury (II) and fibrinogen, mercury (II) and heparinase, mercury (II) and Factor VIIa, mercury (II) and Factor VIII, mercury (II) and Factor IXa, mercury (II) and Factor Xa, mercury (II) and Factor XII, mercury (II) and von Willebrand Factor, mercury (II) and a selectin, mercury (II) and a procoagulant venom, mercury (II) and a plasminogen activator inhibitor, mercury (II) and glycoprotein IIb-IIIa, mercury (II) and a protease, mercury (II) and plasma.

Preferred compositions include silver (I) and collagen, and mercury (II) and collagen. A preferred collagen is type I collagen. The collagen may be derived from any source, preferably mammalian and most preferably bovine in origin, but is it not so limiting. Human collagen, and in particular recombinantly-prepared human collagen, is another preferred procoagulant biopolymer.

Of course, the composition may contain a second or additional procoagulant metal ion, or additional procoagulant biopolymer(s). The invention embraces any combination of additional procoagulant metal ions or procoagulant polymers, as well as other excipients, carriers, stabilizers, preservatives and other additives to a hemostatic product normally needed to ensure stability, shelf life, and other commercial consideration. The known bacteriostatic activity of metal ions may provide an endogenous level of preservation in the compositions of the invention; moreover, the bacteriostatic properties are an additional benefit of the present compositions in use in wound care.

Thus, other hemostatic compositions of the invention include, but are not limited to, silver (I) and mercury (II) and collagen, silver (I) and mercury (II) and thrombin, silver (I) and mercury (II) and prothrombin, silver (I) and mercury (II) and fibrin, silver (I) and mercury (II) and fibrinogen, silver (I) and mercury (II) and heparinase, silver (I) and mercury (II) and Factor VIIa, silver (I) and mercury (II) and Factor III, silver (I) and mercury (II) and Factor IXa, silver (I) and mercury (II) and Factor Xa, silver (I) and mercury (II) and Factor XII, silver (I) and mercury (II) and von Willebrand Factor, silver (I) and mercury (II) and a selectin, silver (I) and mercury (II) and a procoagulant venom, silver (I) and mercury (II) and a plasminogen activator inhibitor, silver (I) and mercury (II) and glycoprotein IIb-IIIa, silver (I) and mercury (II) and a protease, silver (I) and mercury (II) and plasma.

The hemostatic composition of the invention may also include a carrier, such as, but not limited to, polyethylene glycol, hyaluronic acid, cellulose, oxidized cellulose, methyl cellulose, or albumin. These may be used to provide a matrix, a suitable viscosity, deliverability, adherence, or other properties desired to be imparted to the compositions herein for easy in application to a wound. Numerous other carrier which impart these characteristics are embraced herein.

The form of the hemostatic composition of the invention may be prepared in any form suitable for use in the intended application. Various carriers and other materials may be provided in the composition to achieve the desired form, in addition to the at least one procoagulant metal ion and at least one procoagulant biopolymer. For example, the composition in the form of a paste may be prepared for application to a surgical site; a thicker paste, or dough, may be molded by the surgeon for application at a site of the removal of a transarterial cannula. A glue may be prepared with hemostatic properties; other forms include a liquid, a lyophilized powder or foam, for application to or in a wound. As will be described in more detail below in reference to devices comprising the hemostatic composition of the invention, the composition may be dried or lyophilized for form a particular shape, such as a plug, that is useful for particular applications, such as placement to stop the bleeding of a removed transarterial cannula. A bandage comprising a composition of the invention may also be provided. All of these various forms and other are embraced by the present invention.

As mentioned above, the invention is also directed to a hemostatic device which comprises a hemostatic composition as described above. The device may be provided in any number of formats useful for the control of bleeding. For example, the composition of the invention may be provided in the form of a plug, for placement in a wound; or provided on a bandage, gauze, cloth, tampon, membrane or sponge, for application to or placement in a wound. Certain materials may be biodegradable and suitable for placement in a closed surgical wound. Other materials may be provided for later removal. Devices for emergency application to hemorrhaging areas or severed arteries may be useful for emergency use.

In another embodiment of the invention, the hemostatic device comprising the composition may be prepared in an asymmetric fashion, of contain components asymmetrically applied, such that blood is restricted from flowing completely through a device. For example, a blood flow altering agent may be provided at the distal part of the device from that to which is applied to the wound, such that blood will not penetrate beyond the device. A bandage may comprise the instant composition on one side, and a blood-impermeant membrane on the other.

The present invention also embraces various methods for the prophylaxis or treatment of bleeding at a site in the body. This method is carried out by the application or placement of a hemostatic composition or a hemostatic device comprising the hemostatic composition of the invention to or in the site. The present invention embraced various methods and means used for the delivery or placement of the device in the site of desired hemostatic activity. The various forms of the composition and of the device are embraced within this method.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

Effect of Silver (I) Ion and Heparinase on Clotting Time of Heparinized Blood

The hemostatic compositions of the invention were evaluated in two different systems. In one system, clotting time of recalcified, citrated whole blood in the presence of the hemostatic composition was determined using a SONO-CLOT Coagulation Analyzer (Sienco Inc., Wheat Ridge Colo.). Other instrumentation for providing clotting data are equally useful. Results were expressed as clotting time in seconds. In a second system, the hemostatic composition was dried on a cellulose matrix (filter paper), and 7 µl aliquot of fresh blood or recalcified citrated whole blood was placed in the cellulose matrix; resulting in the spreading (perfusion) of the applied blood as an enlarging disk. Upon clotting or reduced perfusion, the further spread of the blood ceases. The surface area of the spread blood in $mm^2$ is used as an indication of the clotting rate of the blood. Results are expressed as mean±standard deviation. The number of samples run is indicated at the top of each data column.

Silver (I) ion was provided as silver nitrate, 5% stock solution. It was diluted 100 fold to 0.05%, or in some cases to 0.01% in the clotting studies. In perfusion studies, a 10 µl aliquot of the solution was applied to the filter paper then dried.

Collagen was from Sigma Chemical Co. In the clotting time studies, the final concentration of collagen was 0.1–0.2%. Heparinase was from Haemoscope Corp. and used at a final concentration of 1 U/mL.

Citrated blood anticoagulated with heparin (2 U/mL) was used as a model of the utility of the compositions of the present invention to induce hemostasis in an individual treated with anticoagulants (including fibrinolytics and antiplatelet therapies) as may occur in patients with myocardial infarction, stroke, unstable angina, thrombophlebitis, peripheral vascular disease, traumatic injury, post-surgical patients and those undergoing cancer chemotherapy. Recalcification time was measured.

| Treatment | Clotting time (sec) (n = 5) |
| --- | --- |
| Control | 287 ± 21 |
| Control + silver(I) | 94 ± 35 |
| Control + heparin | 1930 ± 83 |
| Control + heparin + heparinase | 360 ± 22 |
| Control + silver (I) + heparinase | 872 ± 353 |
| Control + silver (I) + heparin + heparinase | 157 ± 30 |

These data show that silver (I) ion is capable of returning the recalcification time of blood towards normal; moreover, in combination with heparinase, is capable of reducing the clotting time to below normal values.

EXAMPLE II

Effect of Silver (I) Ion and Collagen on Blood Perfusion

Recalcified, citrated whole blood was applied to filter paper impregnated with 5% $AgNO_3$, 2% collagen, or the combination of 2.5% silver nitrate and 1% collagen. The size of the blood disk on the paper was measured.

| Study I | |
| --- | --- |
| Treatment | Perfusion (mm) (n = 13) |
| 5% $AgNO_3$ | 18 ± 4 |
| 2% collagen | 35 ± 23 |
| 2.5% $AgNO_3$ + 1% collagen | 7 ± 4 |

| Study II | |
| --- | --- |
| Treatment | Perfusion (mm) (n = 5) |
| 5% $AgNO_3$ | 17 ± 2 |
| 1% $AgNO_3$ | 42 ± 18 |
| 2% collagen | 28 ± 10 |
| 2.5% $AgNO_3$ + 1% collagen | 7 ± 0.4 |
| 0.5% $AgNO_3$ + 1% collagen | 15 ± 5 |

This study shows the effectiveness of the combination of $AgNO_3$ and collagen, and furthermore, that the combination of a lower concentration of silver (I) ion, 0.5%, with collagen (1%) can achieve the hemostatic effect provided by 5% $AgNO_3$ alone.

EXAMPLE IV

Effect of Silver (I) Ion and Collagen on Clotting Time

The final concentrations of the composition in blood is provided below for a similar experiment.

| Treatment | Clotting time (sec) [n = 41] |
| --- | --- |
| Control | 273 ± 46 |
| Control + 1% collagen | 264 ± 37 |
| Control + 0.6 mM AgNO$_3$ | 220 ± 50 |
| Control + 0.3 mM AgNO$_3$ + 0.5% collagen | 178 ± 42 |

This study demonstrates the combined effect of silver (I) ion and collagen on hemostatic measured by clotting time of recalcified, citrated whole blood.

EXAMPLE V

Effect of Silver (I) Ion on Clotting Time of Whole Blood, Platelet-Rich Blood, and Platelet-Poor Blood This study was undertaken using platelet-rich and platelet-poor plasma to simulate an individual with normal and reduced platelet levels.

| Treatment | Clotting time (sec) [n = 8] |
| --- | --- |
| Normal Blood | 262 ± 26 |
| Normal blood + 2.9 mM AgNO$_3$ | 109 ± 20 |
| Platelet Rich Plasma (PRP) | 314 ± 70 |
| PRP + 2.9 mM AgNO$_3$ | 83 ± 29 |
| Platelet Poor Plasma (PPP) | 353 ± 62 |
| PPP + 2.9 mM AgNO$_3$ | 128 ± 32 |

These studies show the effectiveness of silver (I) ion as a hemostatic agent in blood with low platelet numbers.

EXAMPLE VI

Clot Strength After Silver (I) Ion Induced Clotting of Heparinized Blood

Using the SONOCLOT, tracings of heparinized whole blood clotting in the presence of silver (I) ion were obtained. While the clotting time of heparinized blood is shortened from 1930 seconds to 872 seconds in the presence of silver (I) ion, the physical characteristics of the silver-induced clot as shown by the analyzer demonstrates a stronger clot. In non-heparinized blood, the clotting time is shortened from 217 seconds to 81 seconds in the presence of silver; furthermore, the clot is stronger. In a second study, silver (I) ion reduces the clotting time from 588 to 168 seconds, also with a stronger clot.

EXAMPLE VI

Silver (I) Ion and Thrombin Potentiates Clotting Time Compared to Either Alone Thrombin was used at a final concentration of 0.025 U/mL. Silver ion was present at a final concentration of 2.9 mM.

| Treatment | Clotting time (sec) [n = 8] |
| --- | --- |
| Control | 236 ± 38 |
| Control + thrombin | 156 ± 42 |
| Control + silver | 91 ± 14 |
| Control + silver + thrombin | 71 ± 7 |

EXAMPLE VII

Figure 1:
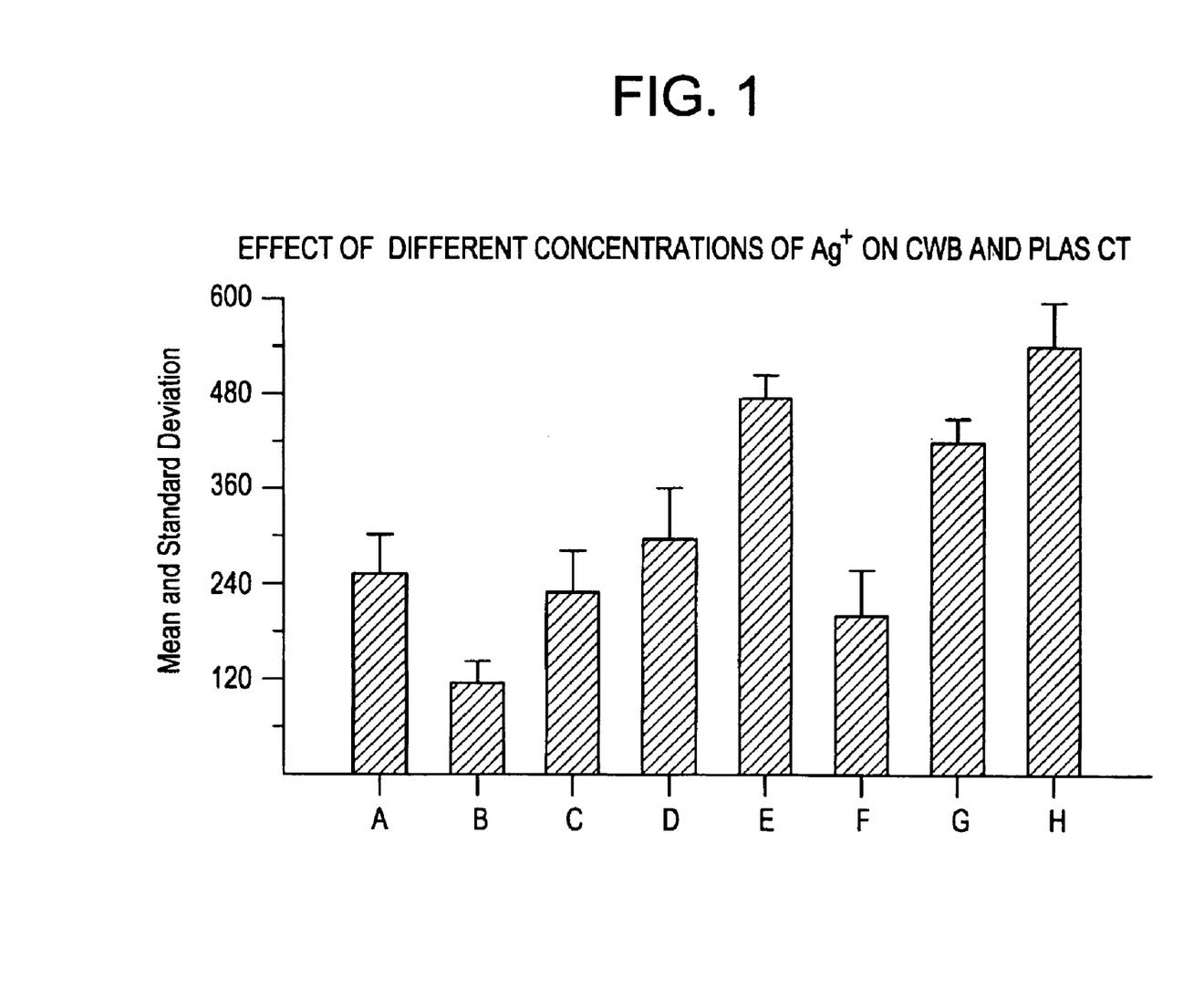
FIG. 1 shows the effect of various concentrations of silver (I) ion on clotting of whole blood and plasma.

Effect of Various Concentrations of Silver (I) Ion on Clotting of Whole Blood and Plasma FIG. 1 depicts the clotting time of citrated whole blood (A-D) and plasma (E-H) in the presence of 0.05% silver (I) ion (B, F), 0.005% silver (I) ion (C, G), 0.0005% silver (I) ion (E, H), or no silver ion (A, E).

EXAMPLE VIII

Figure 2:
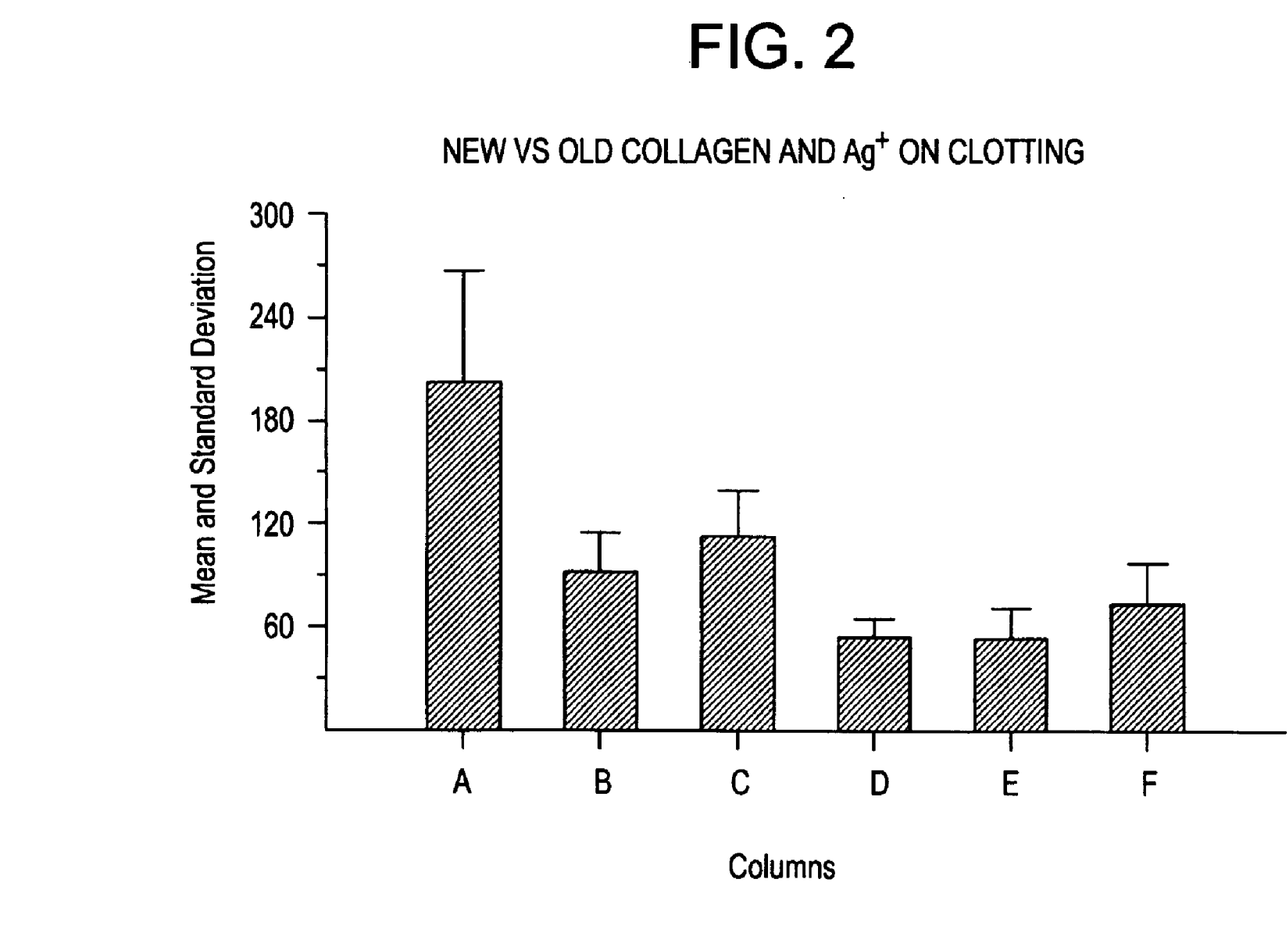
FIG. 2 shows the effect of collagen on clotting of whole blood.

Effect of Collagen Preparations and Silver (I) Ion on Clotting of Whole Blood FIG. 2 depicts the clotting times of whole blood alone (A) or in the presence of 1 mg/ml sponge collagen (B), 1 mg/ml fibrillar collagen (C), 0.05% silver (I) ion (D), 0.05% silver (I) ion and 1 mg/ml sponge collagen (E), and 0.05% silver (I) ion and 1 mg/ml fibrillar collagen (F).

EXAMPLE IX

Effect of Collagen and Silver Ion on Clotting of Heparinized Whole Blood

Figure 3:
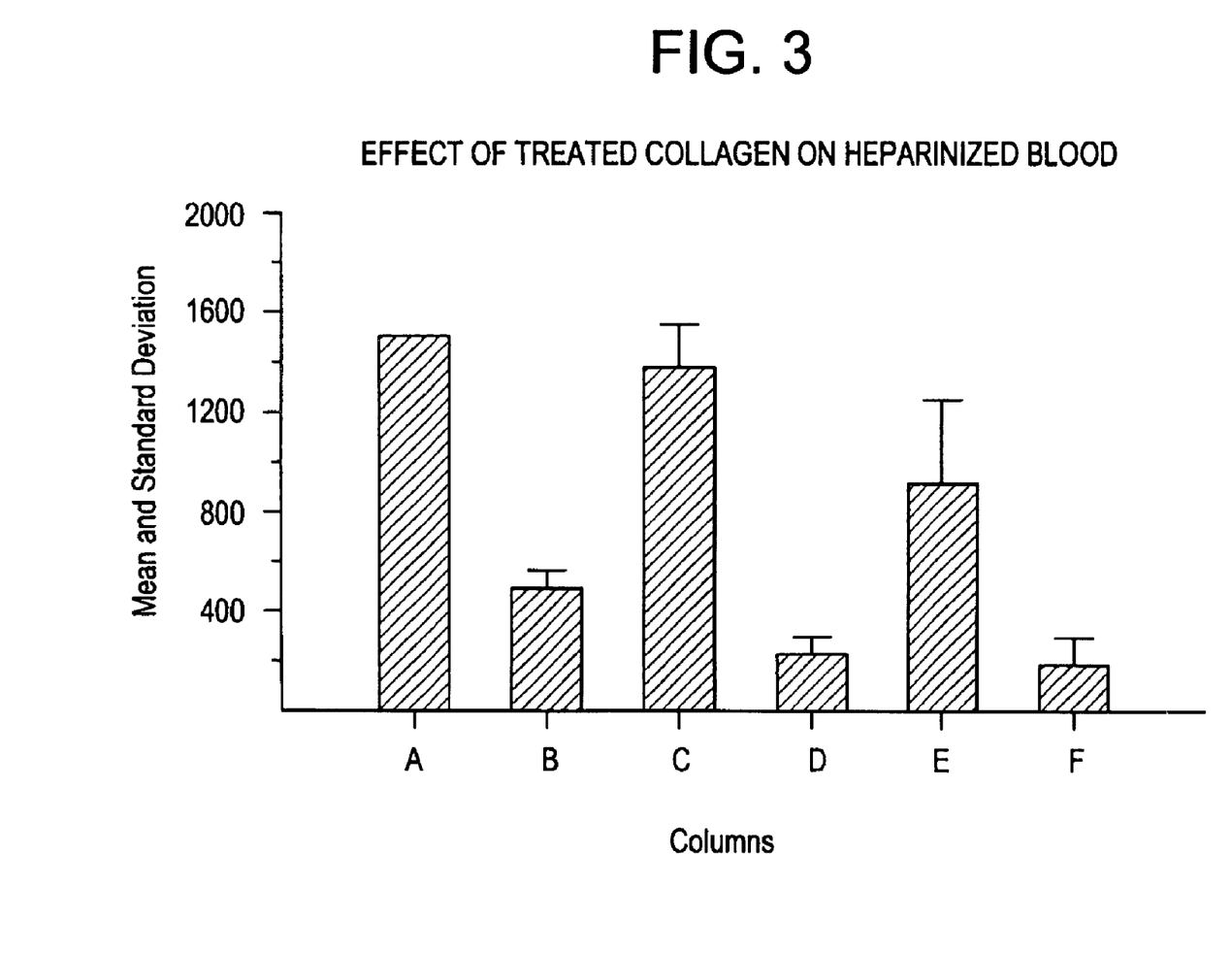
FIG. 3 shows the effect of silver (I) ion and collagen on the clotting of heparinized whole blood.

FIG. 3 shows the clotting times of heparinized whole blood (1 U/ml) alone (A) or in combination with 0.05% silver (I) ion (B), with 1 mg/ml fibrillar collagen (C), and in the presence of the combination of 0.05% silver (I) ion and 1 mg/ml sponge collagen (D). Bar E shows the clotting time of the heparinized whole blood with 1 mg/ml sponge collagen; and in combination with 0.05% silver (I) ion in (F).

Figure 4:
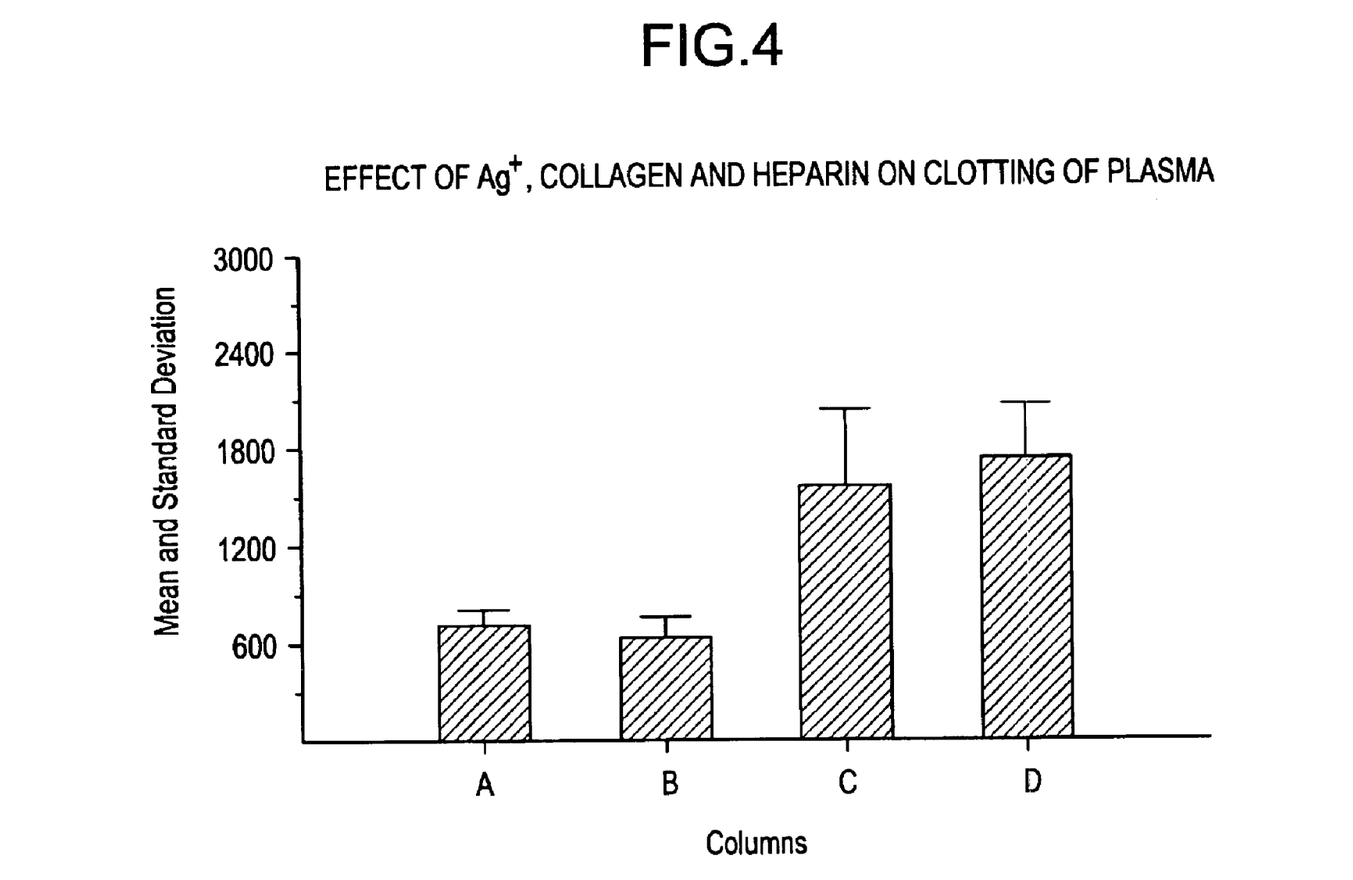
FIG. 4 shows the effect of silver (I) ion and collagen on the clotting of heparinized plasma.

FIG. 4 similarly shows the effect on heparinized whole blood clotting time in the presence of 0.05% silver (I) ion, collagen and 0.25 U/ml heparin (A), and under similar conditions with 0.3% silver (I) ion (B). However, in the absence of collagen at either silver (I) levels, a prolonged clotting time is seen C and D, respectively.

Figure 5:
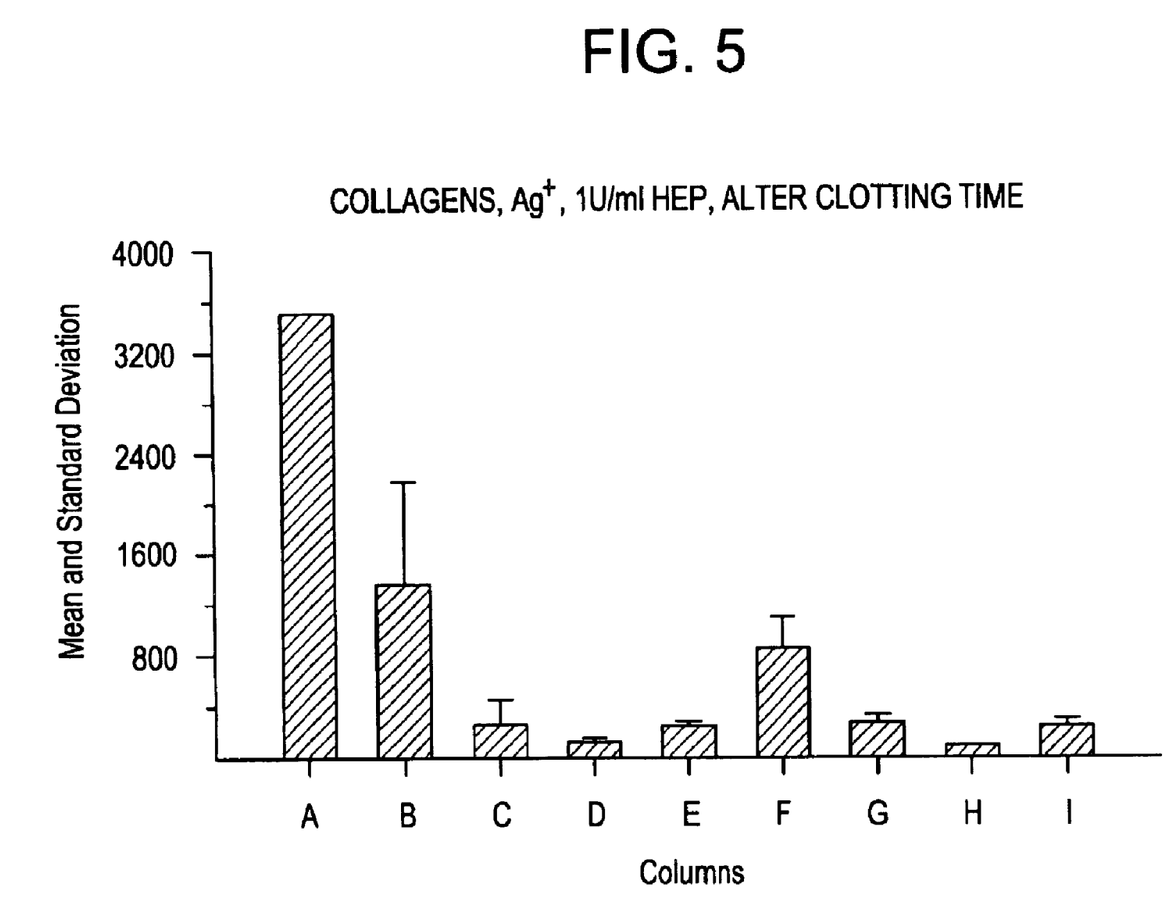
FIG. 5 shows further the effect of silver (I) ion and collagen on the clotting of heparinized plasma.

FIG. 5 shows the clotting time of heparinized whole blood (1 U/ml) with various concentrations of silver ion or mercuric ion. Heparinized whole blood alone (A), with sponge collagen (B), with sponge collagen and 0.05% silver (I) ion (C), with sponge collagen and 0.3% silver (I) ion (D), or with sponge collagen and 0.1% mercuric (II) ion (E). The same series with fibrillar collagen are shown in F-I, respectively.

Figure 6:
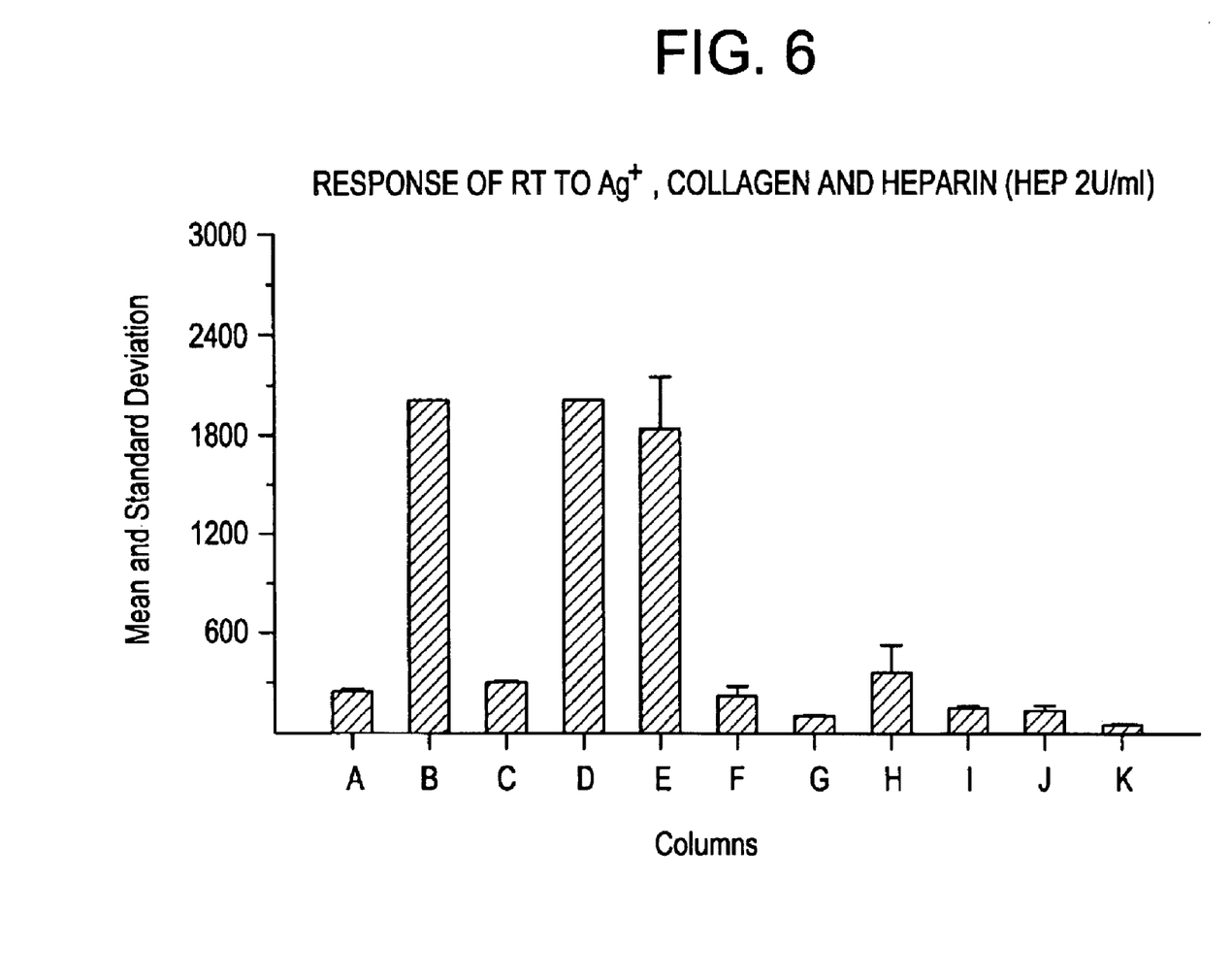
FIG. 6 shows further the effect of silver (I) ion and collagen on clotting of whole blood.

FIG. 6 shows the clotting time of heparinized whole blood (2 U/ml): whole blood (A), heparinized whole blood (B), activated clotting time of heparinized whole blood (C), clotting time of heparinized whole blood plus fibrous collagen (D), or sponge collagen (E); the clotting time of heparinized whole blood with fibrous collagen and 0.05% silver (I) ion (F), the same with 0.5% silver (I) ion (G), or sponge collagen collagen with 0.05% silver (I) ion (H) or 0.5% silver (I) ion (I). Heparinized whole blood with 0.05% silver (I) ion is shown in J, and with 0.5% silver (I) ion in K.

Figure 7:
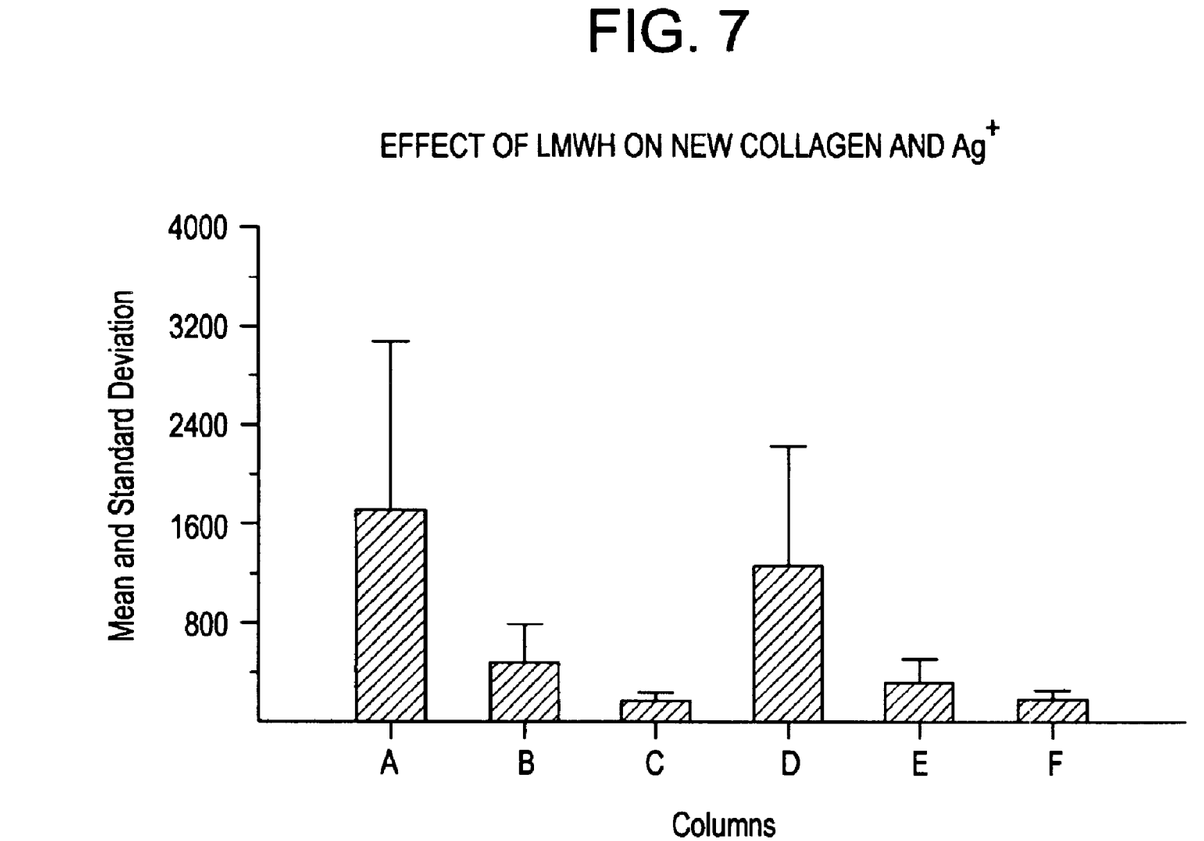
FIG. 7 shows the effect of silver (I) and collagen on clotting time of whole blood with low molecular weight heparin.

FIG. 7 shows the effect of low molecular weight (LMW) heparin and fibrous collagen on clotting time of whole blood. LMW heparinized whole blood (A), with 0.05% silver (I) ion (B), with 0.3% silver (I) ion (C), LMW heparinized whole blood plus fibrous collagen (D), the same plus 0.05% silver (I) ion (E), or with 0.5% silver (I) ion (F).

The foregoing studies demonstrate the effect of the combination of a procoagulant polymer, sponge (cross-linked) or fibrous collagen, and silver (I) or mercury (II) ion, on promoting coagulation of plasma, whole blood, and heparinized plasma and whole blood.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A hemostatic composition comprising at least one procoagulant biopolymer in combination with a procoagulant metal ion, said procoagulant metal ion present in said composition at a level below its effective hemostatic concentration in the absence of said procoagulant biopolymer wherein the hemostatic composition is selected ftom the group consisting of silver (I) and collagen, silver (I) and thrombin, silver (I) and prothrombin, silver (I) and fibrin, silver (I) and fibrinogen, silver (I) and heparinase, silver (I) and Factor VIIa, silver (I) and Factor VIII, silver (I) and Factor IXa, silver (I) and Factor Xa, silver (I) and Factor XII, silver (I) and von Willebrand Factor, silver (I) and a selectin, silver (I) and a procoagulant venom, silver (I) and a plasminogen activator inhibitor, silver (I) and glycoprotein IIb-IIIa, silver (I) and a protease, silver (I) and plasma, mercury (II) and collagen, mercury (II) and thrombin, mercury (II) and prothrombin, mercury (II) and fibrin, mercury (II) and fibrinogen, mercury (II) and heparinase, mercury (II) and Factor VIIa, mercury (II) and Factor VIII, mercury (II) and Factor IXa, mercury (II) and Factor Xa, mercury (II) and Factor XII, mercury (II) and von Willebrand Factor, mercury (II) and a selectin, mercury (II) and a procoagulant venom, mercury (II) and a plasminogen activator inhibitor, mercury (II) and glycoprotein IIb-IIIa, mercury (II) and a protease, and mercury (II) and plasma.

2. A method for the prophylaxis or treatment of bleeding at a site comprising applying to said site a hemostatic composition selected from the group consisting of silver (I) and collagen, silver (I) and thrombin, silver (I) and prothrombin, silver (I) and fibrin, silver (I) and fibrinogen, silver (I) and heparinase, silver (I) and Factor VIIa, silver (I) and Factor VIII, silver (I) and Factor IXa, silver (I) and Factor Xa, silver (I) and Factor XII, silver (I) and von Willebrand Factor, silver (I) and a selectin, silver (I) and a procoagulant venom, silver (I) and a plasminogen activator inhibitor, silver (I) and glycoprotein IIb-IIIa, silver (I) and a protease, silver (I) and plasma, mercury (II) and collagen, mercury (II) and thrombin, mercury (II) and prothrombin, mercury (II) and fibrin, mercury (II) and fibrinogen, mercury (II) and heparinase, mercury (II) and Factor VIIa, mercury (fl) and Factor VIII, mercury (II) and Factor IXa, mercury (II) and Factor Xa, mercury (II) and Factor XII, mercury (II) and von Willebrand Factor, mercury (II) and a selectin, mercury (II) and a procoagulant venom, mercury (II) and a plasminogen activator inhibitor, mercury (II) and glycoprotein IIb-IIIa, mercury (II) and a protease, and mercury (II) and plasma.

3. The method of claim 2 wherein said at least one procagulant biopolymer is selected from the group consisting of collagen thrombin, prothrombin, fibrin, fibrinogen, heparinase, Factor VIIa, Factory VIII, Factory IXa, Factory Xa, Factory XII, von Willebrand Factory, a selsctin, a procogulant vemon, a plasminogen activator inhibitor, glycoprotein IIb-IIIa, a proteases and plasma.

* * * * *